US009895050B2

(12) United States Patent
Gu (10) Patent No.: US 9,895,050 B2
(45) Date of Patent: Feb. 20, 2018

(54) MAIN OPTICAL SYSTEM FOR ENDOSCOPE (71) Applicant: QingDao O-Mec Medical Technology Co., Ltd., Shandong (CN)

(72) Inventor: Changming Gu, Shandong (CN)

(73) Assignee: Qingdao O-Mec Medical Technology, Shandong (CN)

( * ) Notice: Subject to any disclaimer, the term of this patent is extended or adjusted under 35 U.S.C. 154(b) by 0 days.

(21) Appl. No.: 14/907,754

(22) PCT Filed: Jan. 14, 2015

(86) PCT No.: PCT/CN2015/070648
§ 371 (c)(1),
(2) Date: Jan. 26, 2016

(87) PCT Pub. No.: WO2015/135390
PCT Pub. Date: Sep. 17, 2015

(65) Prior Publication Data
US 2016/0174808 A1 Jun. 23, 2016

(30) Foreign Application Priority Data
Mar. 14, 2014 (CN) .......................... 2014 1 0094291

(51) Int. Cl.
*G02B 23/24* (2006.01)
*A61B 1/002* (2006.01)
(Continued)

(52) U.S. Cl.
CPC .......... *A61B 1/002* (2013.01); *A61B 1/00096* (2013.01); *A61B 1/04* (2013.01);
(Continued)

(58) Field of Classification Search
CPC .......... A61B 1/002; A61B 1/313; A61B 1/04; A61B 1/0638; A61B 1/00096;
(Continued)

(56) References Cited

U.S. PATENT DOCUMENTS 7,586,679 B2 * 9/2009 Lei ..................... G02B 23/2446
359/434
2010/0014161 A1 * 1/2010 Kasai ..................... A61B 1/002
359/434

FOREIGN PATENT DOCUMENTS

CN        2855312 Y    1/2007
CN      200987662 Y   12/2007
(Continued)

OTHER PUBLICATIONS

ISR report for PCT/CN2015/070648 completed Mar. 24, 2015.

Primary Examiner — Joseph P Martinez
(74) Attorney, Agent, or Firm — Schmeiser, Olsen & Watts LLP (57) ABSTRACT

This invention relates to a main optical system for an endoscope, in particular, to a main optical system for an endoscope that is focally imaging in the visible and near-infrared lights, which belongs to the technical field of minimally invasive surgery. The used approach is: the objective lens set has a positive off-focus and positive field curvature. The steering set has the negative off-focus and negative field curvature. Moreover, a field lens set is added between the objective lens set and the steering set. The field lens set is located near the focus of the objective lens set. After the field lens is combined with the objective lens set, it will have the positive off-focus and positive field curvature that match to the steering set so that the 850 m defocus amount is less than 0.05 mm and the edge field curvature is less than 0.1 mm in the main endoscope optical system. The system is good in imaging. The invention controls the defocus amount and field curvature in the infrared and visible light bands by offsetting the negative and positive defocus amount and field curvature of the objective lens set, field lens set and steering set; it ensures the imaging quality of the main endoscope optical system and effectively (Continued)

addresses the shortcoming that it is difficult to realize the image difference correction within the broad spectral range for the objective lens set and steering sets independently; it has the advantages, such as more simpler processing, better control precision and lower cost, etc comparing the structure of used steering set and the traditional HOPKINS steering system; and it is especially applicable to the minimally invasive surgery under the infrared fluorescent lights, thus addressing the problems of repeated refocusing in traditional endoscope used for such operation.

3 Claims, 6 Drawing Sheets

(51) Int. Cl.
*A61B 1/00* (2006.01)
*A61B 1/04* (2006.01)
*A61B 1/06* (2006.01)
*A61B 1/313* (2006.01)
*G02B 13/00* (2006.01)
*G02B 13/14* (2006.01)

(52) U.S. Cl.
CPC ............ *A61B 1/043* (2013.01); *A61B 1/0638* (2013.01); *A61B 1/313* (2013.01); *G02B 13/0095* (2013.01); *G02B 13/146* (2013.01); *G02B 23/243* (2013.01); *G02B 23/2446* (2013.01)

(58) Field of Classification Search
CPC .. A61B 1/043; G02B 13/146; G02B 23/2446; G02B 13/0095; G02B 23/243
See application file for complete search history.

(56) References Cited

FOREIGN PATENT DOCUMENTS

| | | |
|---|---|---|
| CN | 101726832 B | 9/2011 |
| CN | 202916487 U | 5/2013 |

* cited by examiner

MAIN OPTICAL SYSTEM FOR ENDOSCOPE

TECHNICAL FIELD

This invention relates to a main optical system for an endoscope, in particular, to a main optical system for an endoscope that is focally imaging in the visible and near-infrared lights, which belongs to the technical field of minimally invasive surgery.

BACKGROUND TECHNIQUE

The medical endoscope has been used more and more widely as an important part of minimally invasive surgery. With the gradual development of minimally invasive surgery technology, a higher technical requirement has been put forward, for instance, a more promising application is currently to add the near-infrared fluorescence analysis technology in the minimally invasive procedure. This requires that the endoscope system must be equipped with a wide spectral imaging ability, must yield imaging simultaneously in the visible (400 nm-700 nm) and near-infrared (700 nm-900 nm) lights and must ensure the focal imaging in the visible and near-infrared lights. At present, the traditional endoscope system can yield imaging in the visible and near infrared lights, however, there is an off-focal distance 0.3 mm-0.5 mm between the near infrared imaging location and the visible light imaging location, which results in refocusing at the observation of the infrared fluorescence image. Refocusing will affect the doctor's operational efficiency each time as the doctor must repeatedly switch the visible light images and near-infrared fluorescent images during the surgery procedure. Therefore, there must be an endoscope system that yields the visible and near infrared images to meet the operational requirements for doctors during surgery procedures.

The endoscopic imaging system consists essentially of an endoscope optical system, a camera adapter optical system and an image sensor. The endoscope optical system consists of a main endoscope optical system and an eyepiece optical system. The main endoscope optical system is composed by an objective lens set and a steering set. The imaging quality of the endoscope is determined by the imaging quality of the main optical system. The objective lens set images the operational field into the focal plane of the objective lens set. The steering set is composed by a HOPKINS rod lens system with an odd array of amplification rate by −1 time. The steering set is designed to transfer the images yielded by the objective lens set to the final image plane of the steering set in 1:1 to ensure the adequate working length of the endoscope. The images yielded in the operational field by the main endoscope optical system becomes the virtual images after the eyepiece optical system. The camera adapter optical system projects the virtual images onto the image sensors. The images in the operational fields are sent to the monitor via circuits and software for doctor's observation.

To achieve parfocality, the entire endoscope imaging system must focus in various components under the visible and near-infrared lights. Specifically, the main endoscope optical system, the eyepiece optical system and the camera adapter optical system must be parfocal. The parfocality is judged by the defocus amount. Pertinent to this application, the defocus amount in the near infrared and visible lights can be defined as: the axial distance between the imaging location of central view field at near Infrared 850 nm wavelength and the imaging location of the central view field at the visible light 550 nm wavelength is an 850 nm defocus amount of the central view field. To simplify the description, the after-said defocus amount refers to the defocus amount of the central view field between the near infrared 850 nm and visible light 550 nm. The analysis finds that the eyepiece optical system and the camera adapter optical system have the defocus amount less than 0.02 mm when the main endoscope optical system achieves the defocus amount less than 0.05 mm and the edge view field curvature less than 0.1 mm; and the entire endoscope system can achieve the parfocal imaging when the main endoscope optical system achieves the defocus amount less than 0.02 mm and the edge view field curvature less than 0.02 mm.

It is easy to achieve the defocus amount less than 0.02 mm and edge view field curvature less than 0.02 mm in the eyepiece optical system and the camera adapter optical system, however, it is very difficult to achieve is to achieve the defocus amount less than 0.05 mm and edge view field curvature less than 0.1 mm in the main endoscope optical system. Concurrently, no literature has reported to meet the requirements.

CONTENTS OF THE INVENTION

The technical problem to be solved by the invention is to provide a main endoscope optical system that yields focal imaging in the visible light (400 nm-700 nm) and near infrared light (700 nm-900 nm). The used approach is: the objective lens set has a positive off-focus and positive view field curvature. The steering set has the negative off-focus and negative view field curvature. A field lens set is added between the objective lens set and the steering sets. The field lens set is located near the focus of the objective lens set. After the field lens is combined with the objective lens set, it will have the positive off-focus and positive field curvature that match to the steering set so that the 850 m defocus amount is less than 0.05 mm and the edge field curvature is less than 0.1 mm in the main endoscope optical system. The system is good in imaging.

The technical scheme of the invention to be detailed in combination of drawings

Figure 1:
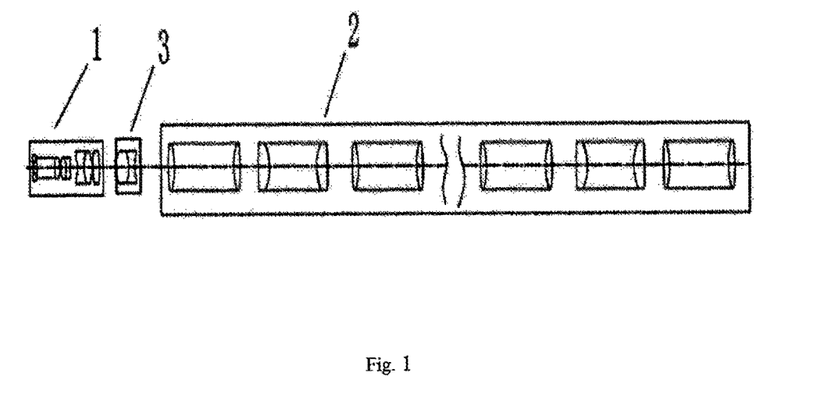
FIG. 1 is a structural schematic drawing for the main endoscope optical system in the invention
Figure 2:
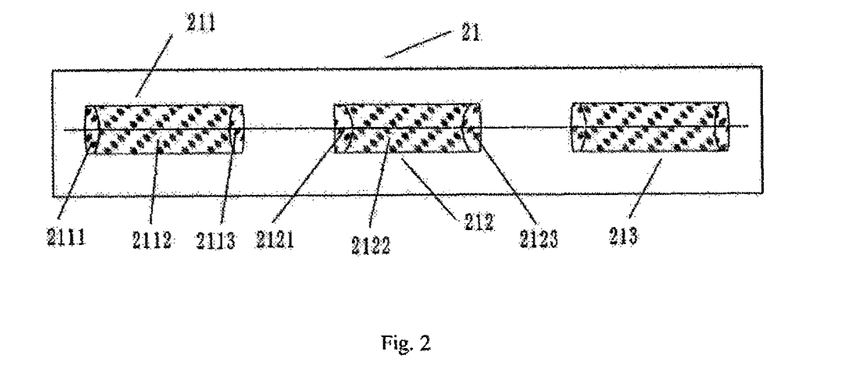
FIG. 2 is a structural schematic drawing for the rod lens steering system 21 by −1 time
Figure 3:
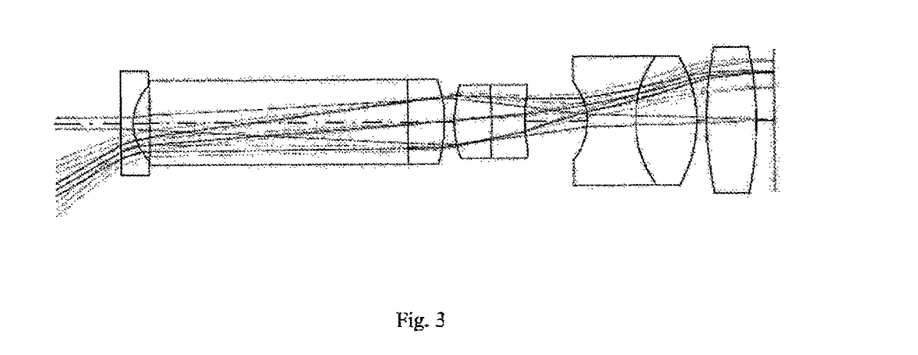
FIG. 3 is a schematic drawing for objective lens structure and imaging principles in the embodiment
Figure 4:
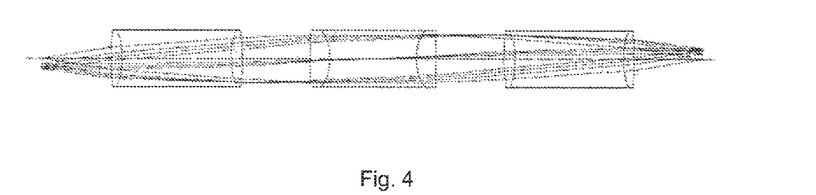
FIG. 4 is a structural schematic drawing for the rod lens steering system 21 by −1 time in the embodiment
Figure 5:
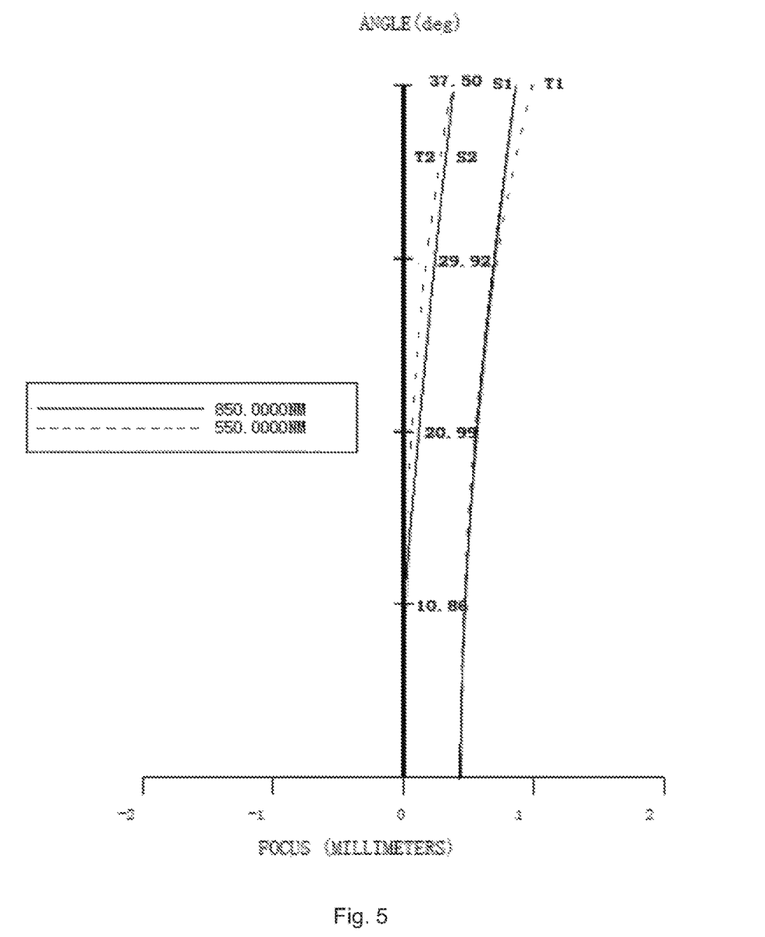
FIG. 5 is a schematic drawing for defocus amount and field curvature of objective lens 1 in the embodiment
Figure 6:
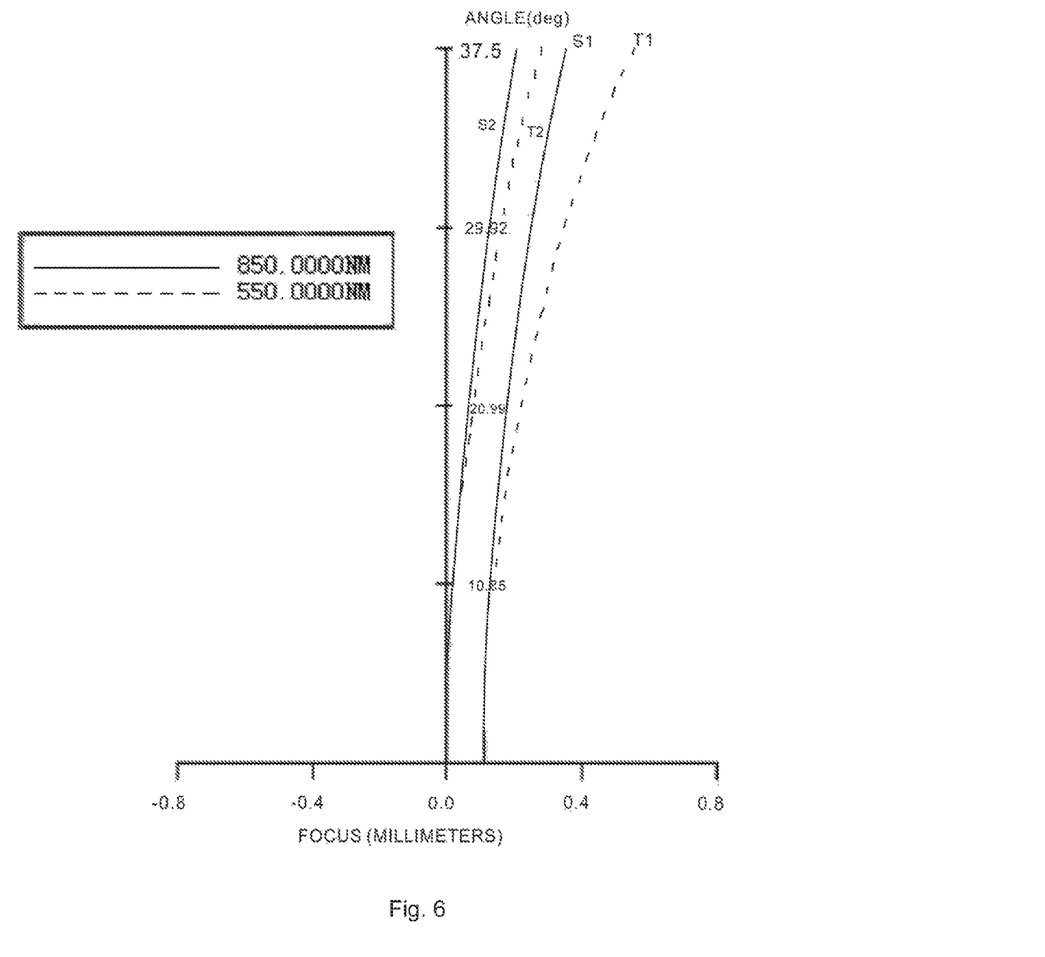
FIG. 6 is a schematic drawing for defocus amount and field curvature after the objective lens 1 and field lens 3 are combined
Figure 7:
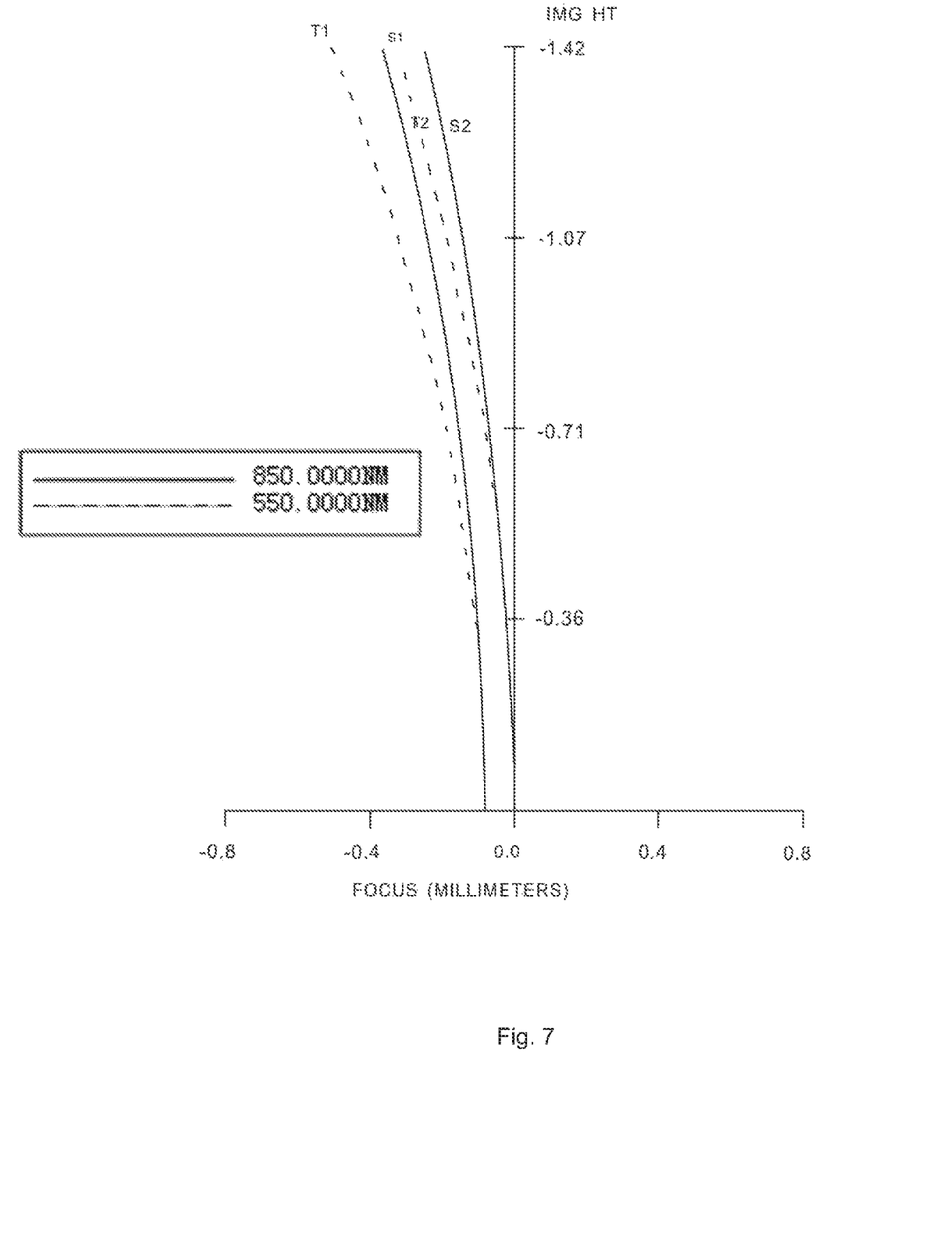
FIG. 7 is a schematic drawing for defocus amount and field curvature of steering set 2 in the embodiment

A main endoscope optical system structure that yields images in the visible (400 nm-700 nm) and near infrared (700 nm-900 nm) includes an objective lens group 1, a steering set 2, a field lens set 3, which is characterized in that the objective lens set 1 is an optical lens set. The wavelength 850 nm has a positive field curvature and a positive defocus and the defocus amount is less than 0.5 mm in the imaging plane of the objective lens set 1. The field lens set 3 is placed between the objective lens set 1 and the steering set 2, and located near the imaging place of the objective lens set 1 to form the telecentric virtual images of the objective lens set 1. In the virtual image location, the wavelength 850 nm has a positive defocus amount less than the objective lens set 1, the edge view field has a curvature less than the objective lens set 1, and the steering set 2 is a focus-free system and composed by 3 or 5 sets of identically-structured rod lens steering system 21 by −1 time. The rod lens steering system 21 by −1 time consists of 3 glued lenses, including a front rod lens set 211, a middle rod lens set 212, and a rear lens set 213. The middle rod lens set 212 consists of a positive lens 2121, a negative rod lens 2122 and a positive lens 2123 in a gluing way. The positive lens 2121 and the positive lens 2123 are positive biconvex lens. The positive lens 2121 and the positive lenses 2123 are made from the same material in the same structure and size. The negative rod lens 2122 is negative biconcave lens, which are equal in the spherical curvature radius and has the same curvature radius as the glued planes of the positive lens 2121 and the positive lens 2123. The rear rod lens 213 has the same material, structure and size as the front rod lens 211 and arranged symmetrically against the middle rod lens 212. The front rod lens 211, the middle rod lens 212 and the rear rod lens 213 are arranged in coaxial manner. The distance between front rod lens 211 and the middle rod lens 212 is equal to that between the middle rod lens 212 and the rear rod lens 213. The objective distance and image distance of the rod lens steering system 21 by −1 time are equal. The steering system 21 composed by 3 or 5 sets of rod lens by −1 time is arranged in such a way that the objective plane and image plane are superposed in two adjacent sets of rod lens steering systems 21 by −1 time to form the steering set 2. The steering set 2 has the negative defocus amount and negative field curvature. The defocus amount value is larger than 0.1 mm and the field curvature value is larger than the objective lens set 1. The main endoscope optical system composed by the field lens set 3 and the steering set 2 has the smallest defocus amount and less edge view field curvature. The def-focus amount is less than 0.05 mm and the field curvature is less than 0.1 mm. The transfer function MTF value of the central view field is larger than 0.3 at 150 alignment/mm and the transfer function MTF value of the edge view field is larger than 0.2 at 150 alignment/mm.

The further technology in the technical scheme of the invention is characterized in that the said field lens set 3 is a double-glued crescent lens.

The further technology in the technical scheme of the invention is characterized in that the said front rod lens 211 of the rod lens steering system 21 by −1 time contains a positive lens 211, a negative lens 2122 and a positive lens 2113. The positive lens 21 is a positive biconvex lens and the negative rod lens 2112 is a negative biconcave lens. The positive lens 2113 and the positive lens 2111 have the same material, structure and size fully. The negative lens 2112 has the same curvature radius in both spherical surface and has the same curvature radius as the gluing surfaces of the positive lens 2111 and 2113.

The advantages of the invention are: 1. To control the defocus amount and field curvature in the infrared and visible light bands by offsetting the negative and positive defocus amount and field curvature of the objective lens set, field lens set and steering set; to ensure the imaging quality of the main endoscope optical system and effectively address the shortcoming that it is difficult to realize the image difference correction within the broad spectral range for the objective lens set and steering sets independently; 2) Comparing the structure of used steering set and the traditional HOPKINS steering system, it has the advantages, such as more simpler processing, better control precision and lower cost, etc.

SPECIFIC EMBODIMENT

In the embodiment, a 10 mm main laparoscope optical system with a field angle 75 degrees and the numerical aperture 0.12 in the image side is made as an example to clarify the technical scheme and working principle of the invention. The key data is listed to avoid repetition as the device in the embodiment has the same structure as the said structures in the invention fully.

The objective lens set 1 is structurally illustrated in Drawing 3, including 5 sets of lens. The field lens set 3 is a double-glued crescent lens. The image-transferring set 2 consists of 3 sets of rod lens steering system by −1 time. The rod lens steering system 21 by −1 time is showed schematically in Drawing 4. The front rod lens set 211 contains the positive lens 2111, negative rod lens 2112 and the positive lens 2113. The positive lens 2111 is a biconvex lens. The negative rod lens 2112 is a biconcave lens. The positive lens 2113 has the same material, structure and size as the positive lens 2111. The negative lens 2112 has the same curvature radius in the spherical surface, has the same curvature radius of the glued surface of the positive lens 2111 and 2113. The defocus amount and field curvature curve are illustrated in Drawing 5. The defocus amount and field curvature curve are illustrated in Drawing for the objective lens set 1 and the field lens set 2. The defocus amount and field curvature curve are illustrated in Drawing 7 for the steering set 3. The defocus amount and field curvature curve are illustrated in Drawing 8 for the main endoscope optical system. The transfer function of the main endoscope optical system is illustrated in Drawing 9.

Figure 8:
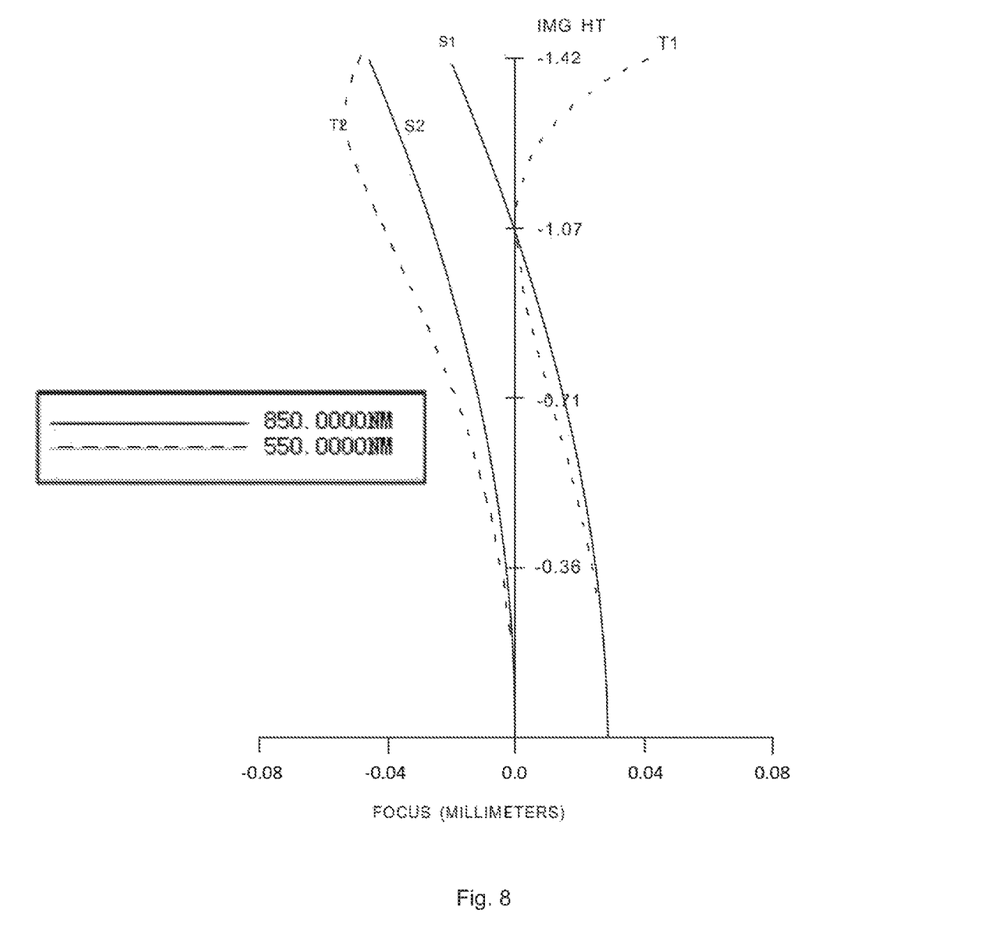
FIG. 8 is a schematic drawing for defocus amount and field curvature of the main endoscope optical system in the embodiment
Figure 9:
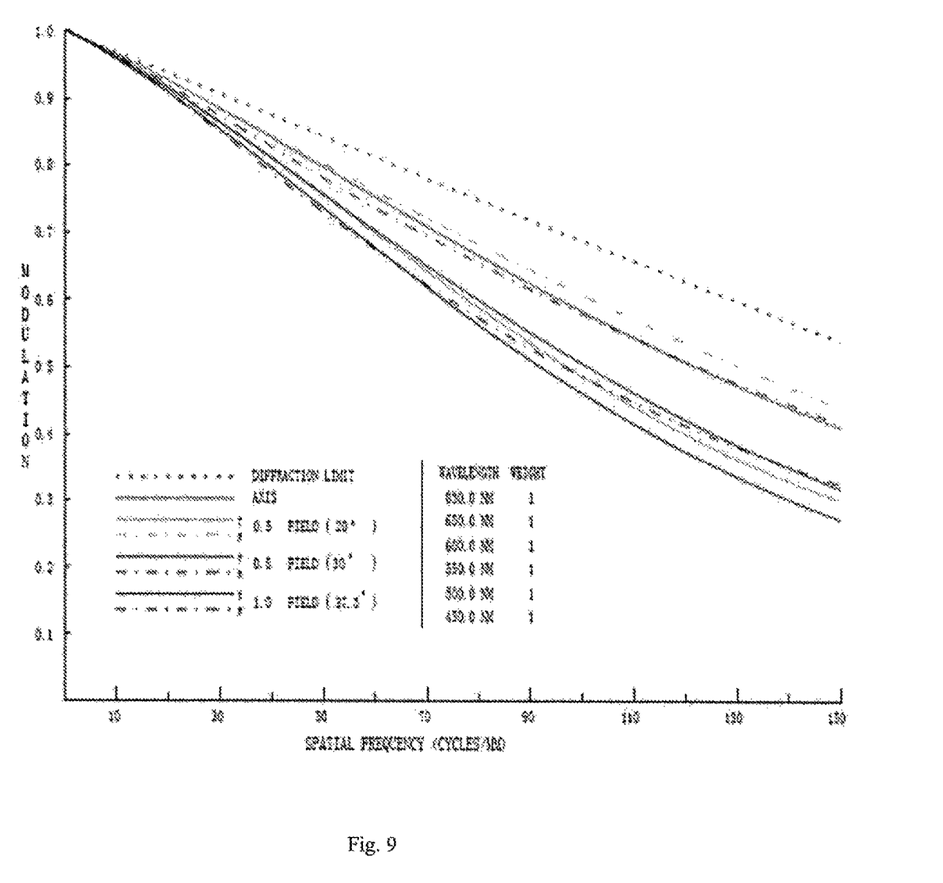
FIG. 9 is a imaging transfer function for the main endoscope optical system in the embodiment

The working principle is: the objective lens set project the images yielded in the operational field onto the rear focal plane of the objective lens set. The image has the positive defocus amount and positive field curvature. The field lens set projects the telecentric images to the objective plane of the image-transferring set. The location of the virtual image is superposed with the steering set whilst the defocus amount and field curvature diminishes. The imaging principle for the rod lens steering system by −1 time is illustrated in drawings. After 3 sets of rod lens steering system by −1 time, the operational field projects the images onto imaging plane of the final set of rod lens steering system by −1 time finally. The rod lens steering system has a negative defocus amount and negative field curvature. The image difference in the same direction will superpose and the image difference in the reverse direction will offset as the optical system combines. Therefore, the system composed by the objective lens set, the field lens set and image-transferring set is combined, the defocus amount and field curvature will offset mutually and the main endoscope optical system has the smallest defocus amount and field curvature. As viewed from the defocus amount and field curvature as well as transfer function drawing of the main endoscope optical system, the device in the embodiment has the smallest defocus amount <0.04 mm and field curvature >0.08 mm. As viewed from the transfer function curve, the system has met the imaging requirements for the HD endoscope system.

The technical scheme of the invention is especially applicable to the minimally invasive surgery under the infrared fluorescent lights, thus addressing the problems of repeated refocusing in traditional endoscope used for such operation.

The invention claimed is:

1. A main endoscope optical system comprising:
an objective lens set with a positive field curvature and a positive 850 nm defocus amount less than 0.5 nm in an imaging plane;
a steering lens set having
either three or five sets of an identically-structured Hopkins rod lens system with a negative defocus larger than 0.1 mm and a negative view field curvature, each rod lens of the rod lens system arranged coaxially and equidistant from each adjacent rod lens, and comprising
a positive bi-convex front rod lens,
a positive bi-convex rear rod lens of the same size and formed from the same material and having the same structure as the front rod lens, and
a negative bi-concave middle rod lens having a matching radius of curvature to the front rod lens and the rear rod lens, glued to the front rod lens and the rear rod lens; and
a field lens set positioned between the objective lens group and the steering lens group, wherein the field lens set is located near a focal point of the objective lens set, and wherein
the field lens set forms a telocentric virtual image of the objective lens group at a 850 nm wavelength virtual image location having a positive defocus amount less than the objective lens group and an edge view field with a curvature less than the objective lens group, wherein
the combined field lens set and objective lens set have a positive defocus equal to the steering lens set and a positive field curvature equal to the steering lens set,
the main endoscope optical system yields parfocal images within a spectrum of between 400 nm and 900 nm having a defocus less than 0.05 mm and an edge field curvature less than 0.1 mm,
a central view field modulation transfer function is larger than 0.3 at 150 alignment/mm, and an edge view field modulation transfer function is larger than 0.2 at 150 alignment/mm,
an objective distance and an image distance of the steering lens set by −1 time are equal and the steering lens set is arranged such that an objective plane and an image plane are superimposed in two adjacent sets of rod lens steering systems by −1 time to form the steering lens set.

2. The main endoscope optical system of claim 1, wherein the field lens set is a double-glued crescent lens.

3. A 10 mm laparoscope optical system comprising:
an objective lens set having five coaxial lenses;
a steering lens set coaxial with the objective lens set having
three sets of rod lenses, each set of rod lenses comprising:
a front rod lens having a positive rod lens,
a negative biconcave lens having a first spherical curvature radius matching a glued surface of the positive rod lens and a second spherical curvature radius matching a second glued surface of the positive lens, and
a positive biconvex lens formed from the same material, structure, and size as the positive rod lens;
a field lens set coaxial with and interposed between the objective lens set and the steering lens set having a double-glued crescent lens, wherein
a field angle of the laparoscope optical system is 75 degrees, and
a numerical aperture of the laparoscope optical system is 0.12 at an image side.

* * * * *